United States Patent
Biskeborn et al.

(10) Patent No.: US 7,640,788 B2
(45) Date of Patent: *Jan. 5, 2010

(54) WEAR GAUGE AND METHOD OF USE

(75) Inventors: Robert Glenn Biskeborn, Hollister, CA (US); Jason Liang, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/364,427

(22) Filed: Feb. 2, 2009

(65) Prior Publication Data

US 2009/0133468 A1    May 28, 2009

Related U.S. Application Data

(62) Division of application No. 10/881,853, filed on Jun. 29, 2004, now Pat. No. 7,509,833.

(51) Int. Cl.
*G01N 3/56* (2006.01)
*B23P 25/00* (2006.01)

(52) U.S. Cl. .......................... 73/7; 29/527.4
(58) Field of Classification Search ............. 73/7; 29/527.4; 356/503

See application file for complete search history.

(56) References Cited

U.S. PATENT DOCUMENTS

| | | | |
|---|---|---|---|
| 3,753,093 A | 8/1973 | Gardner et al. | 324/65 R |
| 4,091,654 A | 5/1978 | Hurtig et al. | 73/7 |
| 4,899,051 A | 2/1990 | Helm | 250/340 |
| 5,905,613 A | 5/1999 | Biskeborn et al. | 360/130.21 |
| 6,080,982 A * | 6/2000 | Cohen | 250/227.11 |
| 6,580,511 B1 * | 6/2003 | Discenzo | 356/477 |
| 7,484,400 B2 * | 2/2009 | Hayashida et al. | 73/7 |
| 7,509,833 B2 | 3/2009 | Biskeborn et al. | 73/7 |

FOREIGN PATENT DOCUMENTS

JP    62-271215    11/1987

(Continued)

OTHER PUBLICATIONS

U.S. Appl. No. 10/881,853, filed on Jun. 29, 2004.

(Continued)

*Primary Examiner*—John Fitzgerald
(74) *Attorney, Agent, or Firm*—Zilka-Kotab, PC

(57) ABSTRACT

A wear gauge is provided for simulating the wear of a magnetic recording component at its interface with a magnetic storage medium comprising a wear gauge block having a wear surface that substantially approximates the geometrical dimensions and contour of the working surface of the magnetic recording component, wherein the wear surface has a coating of transparent material. A test method comprises mounting the wear gauge in a test fixture, positioning a tape and adjusting the over wrap angle at edges of the wear surface, choosing the desired tape tension, speed and runtime, and running the tape, preferably unidirectionally, in operational contact with the wear surface for the desired runtime. The wear surface is inspected under white light illumination to observe and record locations of interferometric color changes on the wear surface. The color changes are correlated to thickness changes of the transparent coating on the wear surface.

16 Claims, 6 Drawing Sheets

FOREIGN PATENT DOCUMENTS

JP 63-163206 7/1988

OTHER PUBLICATIONS

Office Action Summary from U.S. Appl. No. 10/881,853 mailed on Jul. 6, 2005.

Notice of Allowance from U.S. Appl. No. 10/881,853 mailed on Nov. 4, 2005.

Corrected Notice of Allowance from U.S. Appl. No. 10/881,853 mailed on Nov. 14, 2008.

* cited by examiner

WEAR GAUGE AND METHOD OF USE

RELATED APPLICATIONS

This application is a divisional of U.S. patent application Ser. No. 10/881,853, filed Jun. 29, 2004 now U.S. Pat. No. 7,509,833, and which is herein incorporated by reference.

BACKGROUND OF THE INVENTION

1. Field of the Invention

This invention relates to wear gauges, and more particularly, to a wear gauge for measuring tape head wear in a magnetic tape recording system and to a method of measuring tape head contact pressure distribution and wear.

2. Description of the Related Art

In magnetic recording systems, the mechanical interaction of the magnetic head and the recording medium is an important factor determining the performance and reliability of the system. Ideally, the head is in contact or near contact with the moving recording medium to optimize read/write processes. The contact at the head/medium interface results in wear which is a major concern affecting performance and lifetime of both head and medium.

In magnetic tape and disk recording systems, considerable effort has been made to determine the wear resistance of magnetic head materials in contact with the recording media. As recording density increases, knowledge of the head wear characteristics becomes of increased importance, since even very small dimensional changes at the surface of the head can contribute to performance degradation of the recording system.

A common procedure for determining head wear is to run the head for an extended period in operative contact with the moving magnetic medium. For example, U.S. Pat. No. 4,091,654 discloses a method for testing abrasion of a recording head. According to this patent, the smoothness of a simulated head made of polished steel or other material is measured before and after a given amount of contact with a recording surface using a fiber optic emitter/detector to measure light reflected from the surface of the head. However, this type of test does not measure the wear rate or identify specific wear regions on the head.

U.S. Pat. No. 3,753,093 discloses a device for determining the wear rate of a simulated recording head in contact with a moving magnetic tape. The surface of the simulated head contacting the tape has deposited thereon strips of magnetic alloy similar to the alloy of an actual recording head. During the tape transport operation, the increase of the electrical resistance of magnetic alloy strip is monitored to measure the rate of wear of the magnetic alloy strip. This type of test requires a complex procedure for depositing the magnetic alloy strips and electrical contacts and does not provide a good measure of the microscopic wear profile.

There is an ongoing need for a wear gauge and method of use providing a simple and inexpensive tool for evaluating head wear and head/media compliance in magnetic recording systems. The present invention provides an improved wear gauge and method of use addressing this need.

SUMMARY OF THE INVENTION

In accordance with the principles of the present invention, there is disclosed a wear gauge for simulating the wear of a magnetic recording head at its interface with a magnetic storage medium comprising a wear gauge block having a wear surface that substantially approximates the geometrical dimensions and contour of the working surface of the magnetic recording head, wherein the wear surface has a coating of transparent material having appropriate wear characteristics.

A method of testing the wear of a wear gauge simulating a magnetic recording head at the interface of the recording head with a magnetic recording medium is disclosed. The method of testing comprises mounting a wear gauge having a wear surface in a test fixture, positioning a tape and adjusting the wrap or overwrap angle at edges of the wear surface, choosing the desired tape tension, speed and runtime, running the tape preferably unidirectionally in operational contact with the wear surface for the desired runtime, inspecting the wear surface under white light illumination, recording the observed locations of interferometric color changes on the wear surface, converting color changes to thickness changes of a transparent coating oil the wear surface, and running profilometer scans across the wear surface if desired.

The above as well as additional objects, features, and advantages of the present invention will become apparent in the following detailed description.

BRIEF DESCRIPTION OF THE DRAWINGS

For a fuller understanding of the nature and advantages of the present invention, as well as the preferred mode of use, reference should be made to the following detailed description read in conjunction with the accompanying drawings. In the following drawings, like reference numerals designate like or similar parts throughout the drawings.

DETAILED DESCRIPTION OF THE PREFERRED EMBODIMENT

Figure 1:
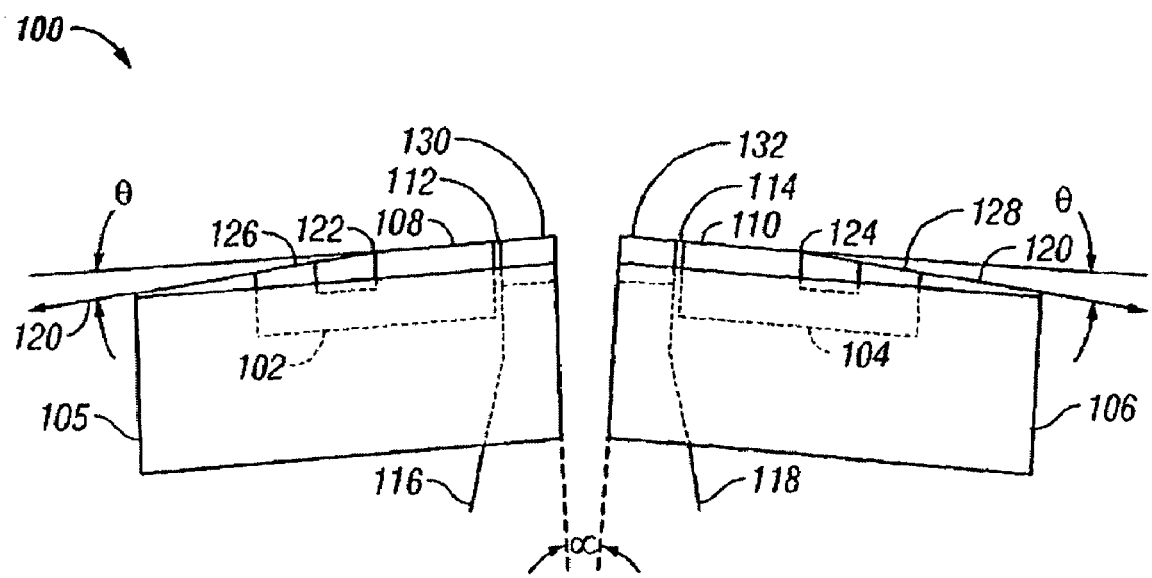
FIG. 1 is an end view, not to scale, of a bi-directional flat contour read/write tape recording head simulated by an embodiment of the wear gauge of the present invention.

FIG. 1 illustrates a prior art bi-directional read-while-write flat contour tape recording head 100. Rowbar substrates 102 and 104 of a wear resistant material, such as the substrate ceramic typically used in magnetic disk drive heads, are mounted in carriers 105 and 106 fixed at a small angle A with respect to each other. The ceramic rowbar substrates 102 and 104 are provided with flat transducing surfaces 108 and 110 and a row of transducers at the surfaces of gaps 112 and 114. Electrical connection cables 116 and 118 connect the transducers to the read/write channel of the associated tape drive. To control the overwrap angle H of the tape 120 at edges 122 and 124, outriggers 126 and 128 lapped at the desired wrap angle are provided. The wrap angle going onto the flat transducing surface is usually between 1/8 degree and 4.5 degrees. The rows of transducers are protected by closures 130 and 132 made of the same or similar ceramic as the rowbar substrates 102 and 104.

Figure 2:
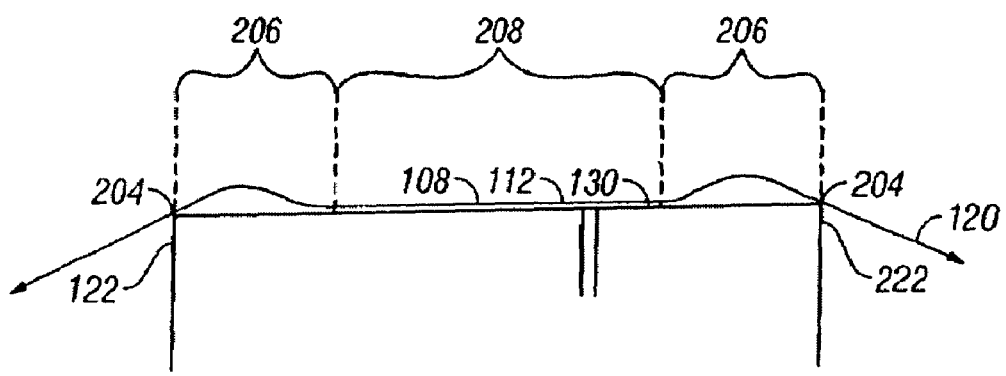
FIG. 2 is an end view, not to scale, depicting the separation of the tape from the transducing surface of the flat contour recording head of FIG. 1.

FIG. 2 illustrates flat transducing surface 108 of the flat contour head 100 of FIG. 1. As the tape 120 moves from left-to-right or from right-to-left over the flat transducing surfaces 108, the tape separation from the transducing surface is different in different zones across the surface. At the edges 122 and 222, the overwrap angle results in bending of the tape to conform to the flat transducing surfaces in a narrow "compression zone" 204 where the tape is in contact with the edges 122 and 222, the compression zone having a effective length of about 0.1-10 microns, increasing to 15-45 microns over the life of the head. By scraping (skiving) the air from the surface of the moving tape, a vacuum forms between the tape and the flat transducing surface holding the tape in contact with the transducing surface; however, bending of the recording tape due to the overwrap results in separation of the tape from the transducing surface in a "canopy zone" 206 for a distance that depends on the wrap angle, the tape thickness and the tape tension and speed. For typical values of tape tension and tape thickness and wrap angles in the range of 1/2-2 degrees, the canopy zone distance is in the range of 20-200 microns. In a "tack-down zone" 208, the vacuum between the tape and the transducing surface is sufficient to overcome this separation and the tape 120 is in contact or near contact with the flat transducing surface 108. In the flat contour head 100, the transducers are positioned at the gaps 112 and 114 in the tack-down zones 208 where the tape is in contact or near contact.

Figure 3A:
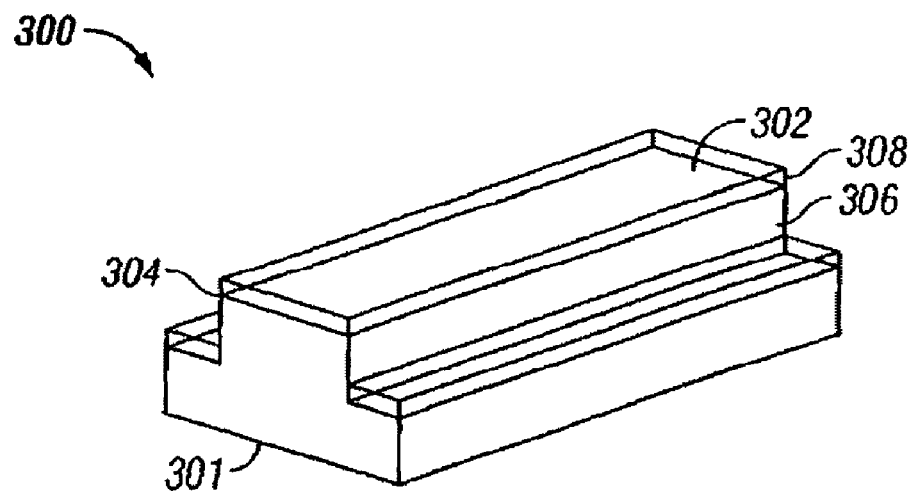
FIG. 3a is a perspective view, not to scale, of an embodiment of the wear gauge of the present invention for use with a magnetic tape recording system.

FIG. 3a is a perspective view of an embodiment of a wear gauge 300 suitable for simulating and measuring the tape-head contact pressure distribution and head surface wear of a flat contour tape head 100 of the type shown in FIGS. 1 and 2. As a result of the variations in tape separation from the transducing surface 108 in different zones the contact pressure distribution and resulting wear of the transducing surface 108 varies across the surface. Use of the wear gauge 300 provides a simple means to measure this non-uniform wear and to derive the contact pressure distribution in this complex wear situation.

Wear gauge 300 is a dummy flat profile head comprising a wear gauge block 301 having a wear surface 302 and air skiving edges 304 and 306. The wear gauge is made of a hard wear resistant material, preferably the ceramic AlTiC used as a substrate for magnetic recording heads. The wear surface 302 of the dummy bead has substantially the same dimensions and edge geometry as the transducing surface (acting surface or working surface) 108 of the tape head 100. The surface 302 has a thin coating 308 of transparent material, preferably $SiO_2$ having a thickness in the range of 50-250 nm. Alternatively, other transparent coatings, including, but not limited to, $Al_2O_3$, amorphous carbon and sapphire may be used. The transparent coating material is preferably chosen to wear more rapidly than the working surface. Thickness changes of the coating 308 due to tape induced wear are measured by observation of optical interference of light reflected from the front and back surfaces of the coating or by surface profilometry measurements across selected regions of the surface.

Figure 3B:
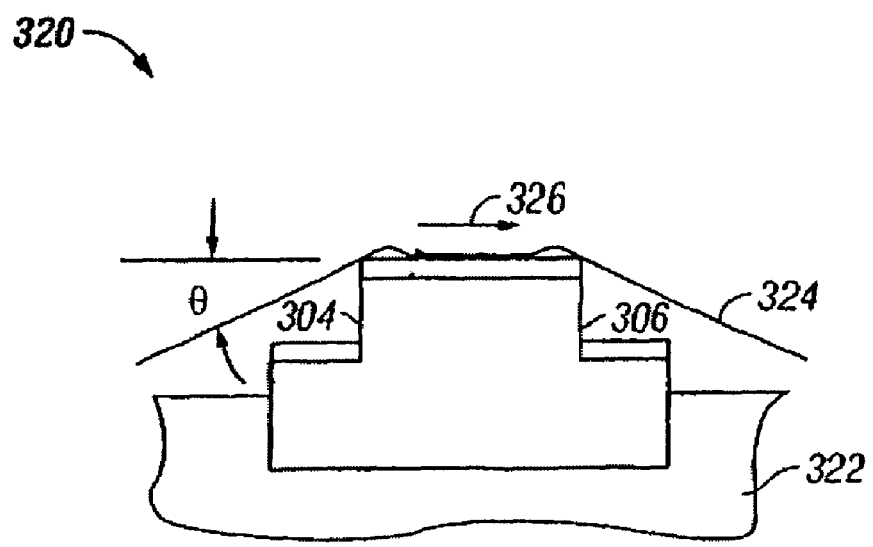
FIG. 3b is a end view, not to scale, of the wear gauge of FIG. 3a showing a magnetic tape interfacing with the gauge.

FIG. 3b illustrates a test fixture 320 showing an end view of the wear gauge 300 mounted in a carrier 322 with a magnetic tape 324 interfacing with the gauge. The tape is shown moving from left to right (indicated by the arrow 326) across the coated wear surface 302. Movement of the tape from right to left may also be used as may bi-directional movement. The overwrap angle H is controlled to a precisely fixed value in the range of 1/8 to 4.5 degrees, and preferably 1 degree, by means (not shown) well known to the art.

Although, the wear gauge described in this embodiment is designed to simulate the wear of a flat contour tape head, a wear gauge according to the principles of this invention can be designed having a contoured wear surface to simulate a contoured tape head. A wear gauge to simulate a tape head having a cylindrical contoured transducing surface is same as wear gauge 300 except that instead of wear surface 302 being flat, the wear surface has a cylindrical contour having curvature in the direction of the tape motion across the head. As with the case for a flat wear surface, the contoured wear surface has a thin coating 308 of transparent material. Alternatively, wear gauges according to the principles of the invention can also be made to simulate wear of other components that interact mechanically with a moving tape, including, but not limited to rollers and guides. Suitable wear gauges for simulating wear of other components may be made by providing a thin coating of transparent material on the working surfaces of the components that interface with the moving tape.

Figure 4:
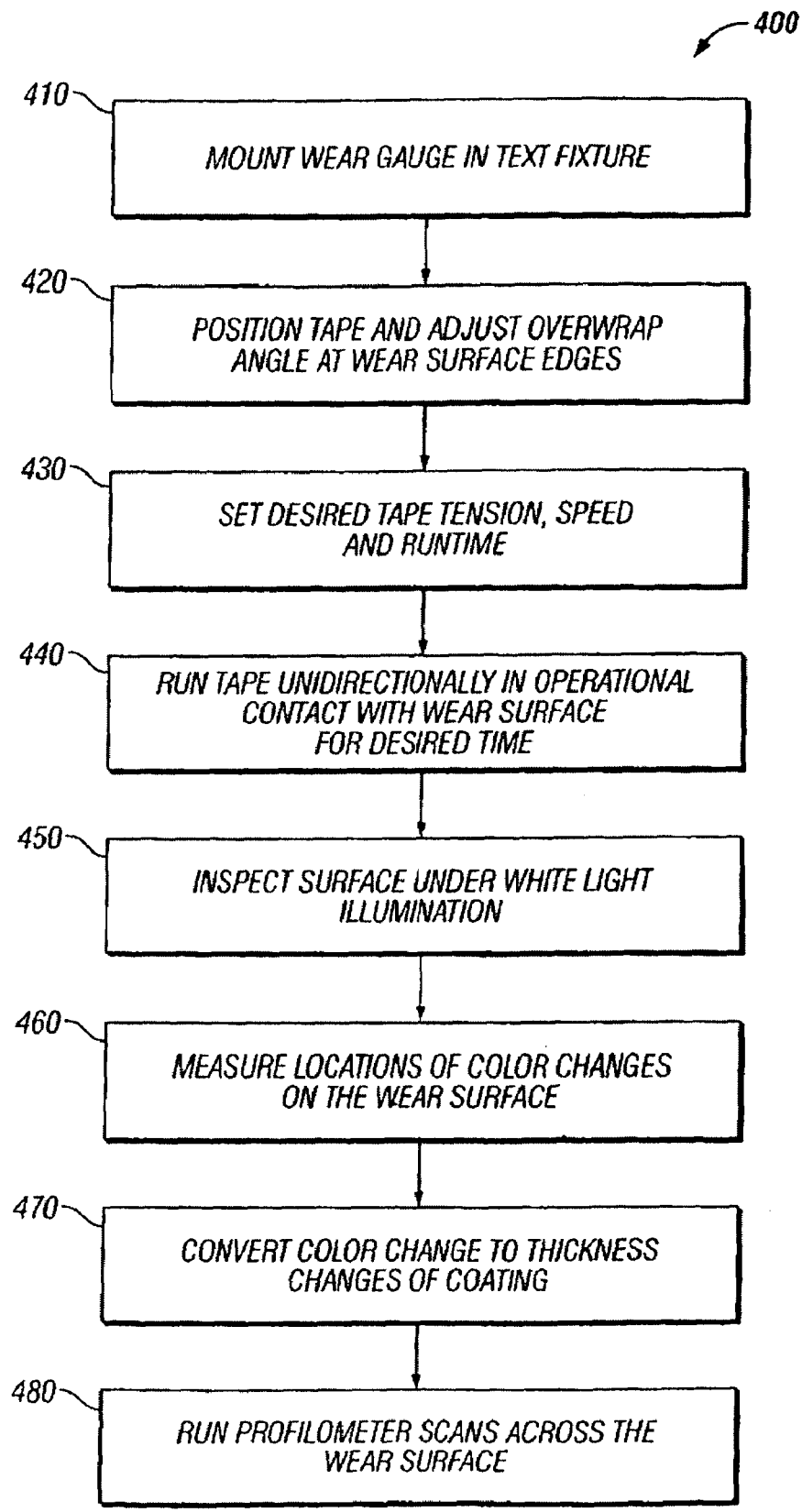
FIG. 4 is a schematic chart showing a method of wear testing employing the wear gauge of the present invention.

A test method 400 according to an embodiment of the invention is illustrated schematically in FIG. 4. The test comprises mounting the wear gauge 300 in the test fixture 320 (step 410), positioning the tape 324 with respect to the wear surface 302 so that the overwrap angle H at edges 304 and 306 is precisely 1 degree (step 420), setting the desired tape tension, speed and runtime (step 430), and running the tape in one direction at a desired tension and speed for a fixed time period (step 440), preferably about 10 hours or more. Unidirectional motion of the tape for runtimes of several hours duration may be achieved by several methods. For tests using a tape cassette of limited tape length, the tape is run to the desired stopping location, is stopped and the head is retracted and the is tape rewound and stopped again. The head is reengaged with the tape and the tape started. This procedure is repeated until sufficient unidirectional runtime is accumulated. Alternatively, instead of retracting the head to disengage it from the tape for rewinds, the tape may be lifted away from the head using movable rollers or by air pressure. Another alternative test method is to use an endless loop of tape to run the wear test. Disadvantages of this method is the need to prepare suitable loops of each tape type to be wear tested and the abrasivity of the tape decreases rapidly during the first few hundred cycles.

At the end of the test run period the contact footprint and wear rates are revealed by changes in the thickness of the coating 308 of $SiO_2$ on wear surface 302. The wear surface 302 is inspected at relatively low magnification under white light illumination incident on the coating 308 (step 450). Thickness variations of the coating are observed and located as color changes due to interference effects of light reflected from the top surface of the coating and light transmitted through the coating and reflected from the wear surface 302 (step 460). Illumination with light at near normal incidence to the plane of the wear surface is preferred since the optical path of the light through the coating is then simply twice the coating thickness. For normal incidence, the retardation of the light reflected from the back surface of a coating having thickness t is 2 nt where n is the index of refraction of the coating.

Since the index of refraction of the coating 308 is known or can be measured, the color changes can be readily converted to thickness changes of the coating using considerations of thin film interference theory well known to the art (step 470). Both constructive interference and destructive interference effects on various spectral components of the incident white light must be considered in making the conversion from observed color to coating thickness. For a coating having an index of refraction less than the index of the substrate material, the condition for destructive interference is that the retardation 2 nt=K/2, where K is the wavelength in air of a spectral component of the light. For constructive interference, the condition is that 2 nt=K. A chart showing observed color of the reflected light as a function of coating thickness may be generated for a particular coating, such as for example $SiO_2$, and the illumination conditions used to inspect the wear gauge. Measurements of the position on the wear surface at which interference colors of the reflected light occur provides a mapping of the variations of coating thickness due to wear. Alternatively, inspection with monochromatic illumination may be used resulting in observation of regions of constructive and destructive interference due to coating thickness changes, however the sensitivity to changes in thickness is reduced due to use of a single wavelength of incident light. Surface profilometry using commercial profilometers as is known to the art is carried out across selected regions of the wear surface 302 to provide quantitative confirmation of the interferometrically derived wear of the coating 308 (step 480). Alternatively, optical profilometry measurements of the coating oil the wear surface may be done by first coating the surface with a thin gold film (gold flashing) as is known to the art.

Figure 5:
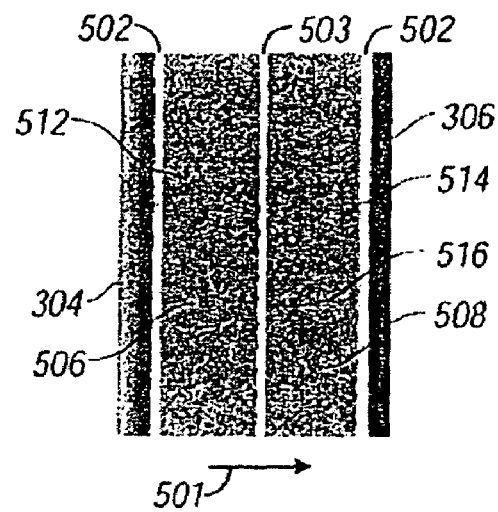
FIG. 5 is a view of the top surface of the wear gauge of the present invention viewed with white light after interaction with a magnetic tape.

FIG. 5 is a black and white rendering of a view in color of the wear surface of a wear gauge under white light illumination depicting thickness changes of the coating 308 after a wear test using a magnetic tape medium. The wear gauge used for this test was a rowbar of a magnetic recording tape head with the transducing surface coated with a layer of $SiO_2$ having a thickness of approximately 75 nm. The direction of tape motion, represented by arrow 501, was from left to right. The narrow bright bands 502 show the wear at the edges 304 and 306 of the wear surface of the wear gauge where the tape overwrap at the surface occurs. The light band 503 was due to the alumina forming the gap in the transducing surface of the ceramic rowbar substrate (FIG. 1). Regions 512 and 514 that correspond to the low contact pressure in the canopy zones 206 discussed above with reference to FIG. 2 appear blue when viewed in color. The low contact pressure in these regions is due to separation of the tape from the transducing surface in a canopy zone region resulting from tape stiffness resisting bending forced by the tape overwrap. A broad region 516 that corresponds the higher contact pressure in the tack-down zone appears magenta when observed in color. In the transition regions between low contact pressure regions 512 and 514 and the higher contact pressure region 516 gradual changes in the coating thickness can be seen as subtle changes of color under white light inspection. Each change of color corresponds to a change of thickness of the coating allowing for a quantification of the wear by visual inspection.

Figure 6:
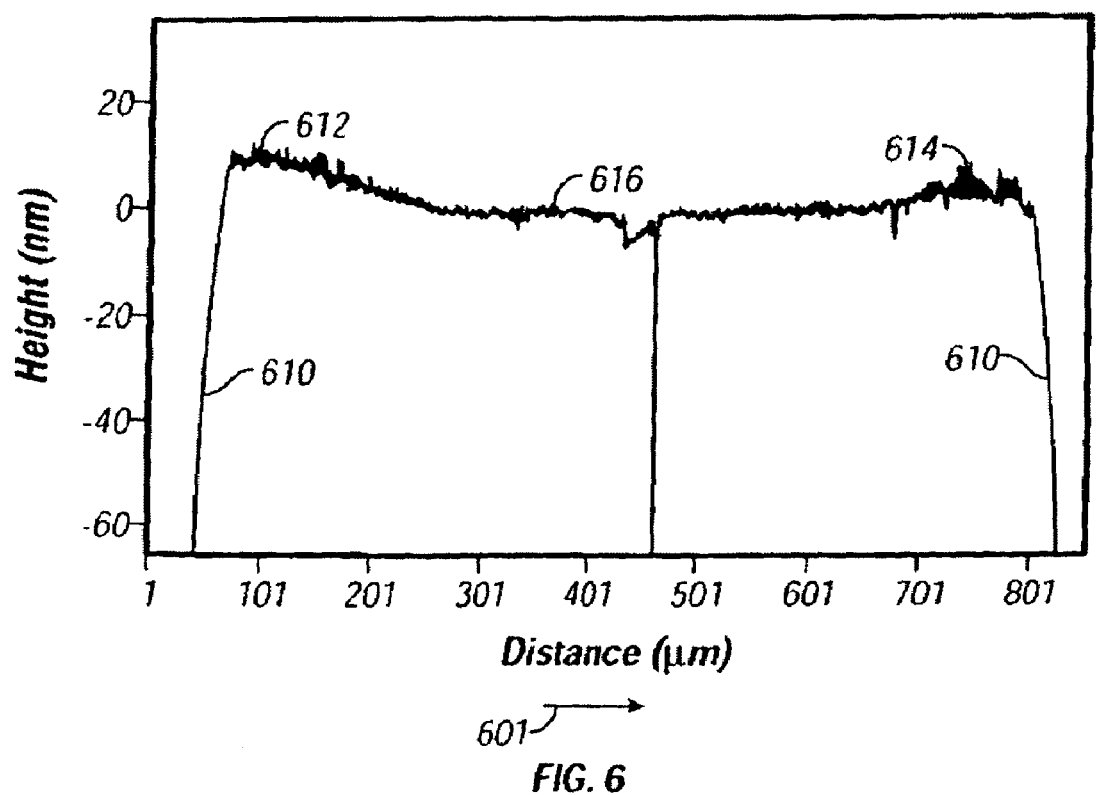
FIG. 6 is a profilometer scan of the top surface of the wear gauge of FIG. 5 after interaction with a magnetic tape.

FIG. 6 shows an exemplary profilometer trace measured across the wear surface of the wear gauge shown in FIG. 5. The direction of tape motion, represented by arrow 601, was from left to right. In FIG. 6, severe wear 610 at the left and right edges of the profile trace correspond to regions of high contact pressure where the tape overwrap occurs. The humps 612 and 614 in the profile trace corresponds low contact pressure in the canopy zone 206 discussed above with reference to FIG. 2 where separation of the tape from the transducing surface in a canopy zone region results from tape stiffness resisting bending forced by the tape overwrap. The gradual thickness decrease (approximately 10 nm) of the $SiO_2$ coating measured in going from the top of the hump 612 toward the broad central region 616 corresponding to the tack-down zone 208 (see FIG. 2) may be observed as gradual color changes due to the interference effects discussed herein above during inspection of the wear gauge under white light illumination.

The profilometry trace of FIG. 6 can be used together with the view in color of the wear surface under white light illumination shown in FIG. 5 to correlate the observed colors of the worn coating with the measured thickness of the coating at the same positions on the wear surface. A calibration graph or chart can be generated of observed color versus coating thickness for the particular coating material being used on the wear surface. If a constant well-controlled coating thickness is used in fabricating the wear gauges, a reference chart of coating color versus amount of wear can be generated. Reference to the latter calibration chart allows quantitative wear of the coatings of future wear gauge tests to be directly determined from the observed colors.

Since the hardness of the $SiO_2$ coating is less than that of the wear surface of a typical magnetic head, use of the wear gauge of the present invention provides an accelerated wear test. Wear tests having a duration of only a few hours simulate the effects of much longer running times of an actual head in a tape recorder system. This accelerated test is often very desirable when running comparative tests of head wear with different tapes and different running conditions such as tape speeds and tape tension.

When running accelerated tests, it is useful to have a method to calibrate the accelerated tests with the actual wear of a head under the same operating conditions. With reference to FIG. 3b, this calibration may be obtained by running the tape over the coated wear block 301 for a time $t_1$ when the coating 302 at edge 304 is just worn through and the tape contacts the wear block material. This point may be detected by grounding the substrate through an ammeter. When the tape breaks through the insulating coating, a small triboelectric current flows. A second test is run on an uncoated wear block and the time $t_2$ for an equal amount of wear to occur at uncoated edge 304 is measured. The ratio $t_2/t_1$ of the edge wear times of the uncoated and coated wear blocks gives the acceleration factor which applies to all the wear across the coated wear surface.

Figure 7A:
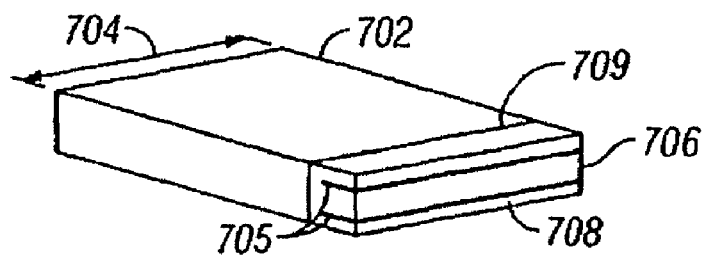
FIG. 7a-c are perspective views, not to scale, of the wear gauge of the present invention at various stages of fabrication by a first method.
Figure 7B:
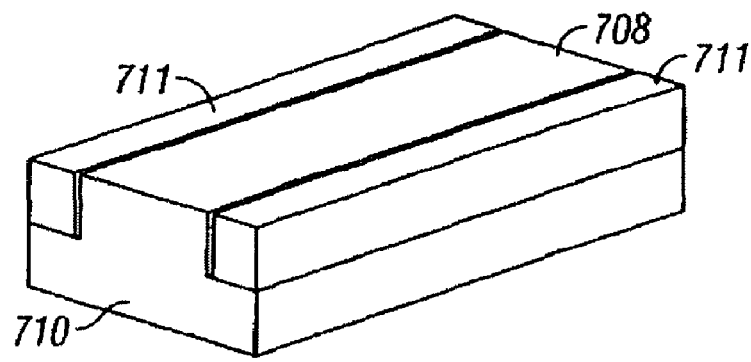
Figure 7C:
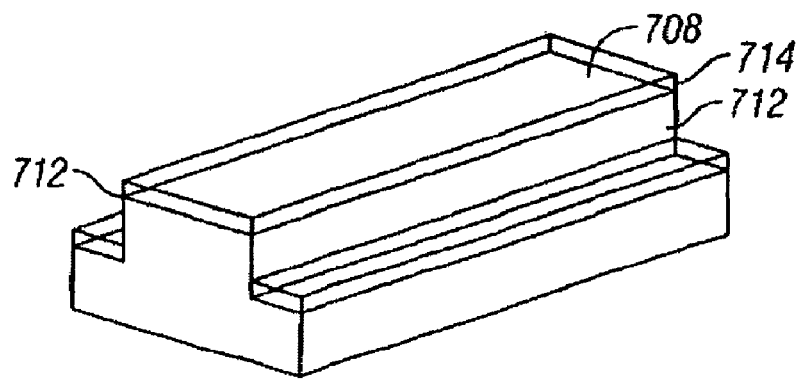
Figure 8A:
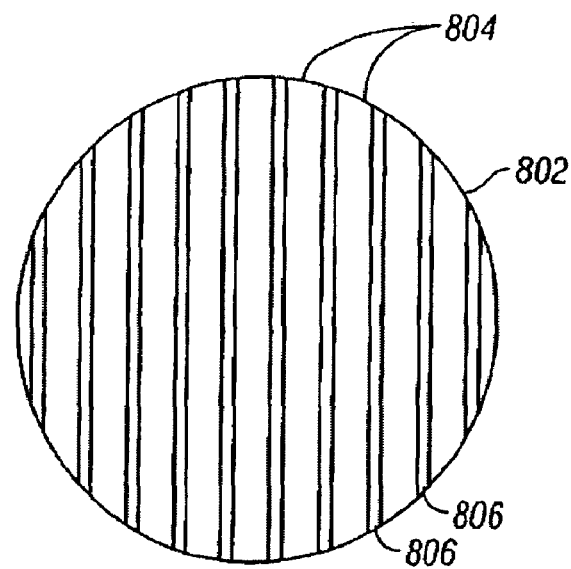
FIG. 8a-d are top and side views, not to scale, of a wafer during steps in fabrication of the wear gauges of the present invention by a second method.
Figure 8B:
Figure 8C:
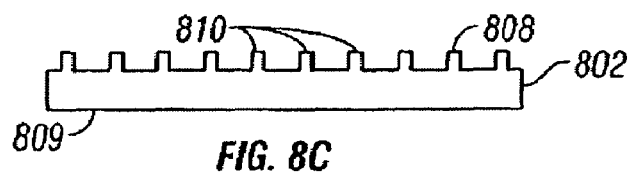
Figure 8D:
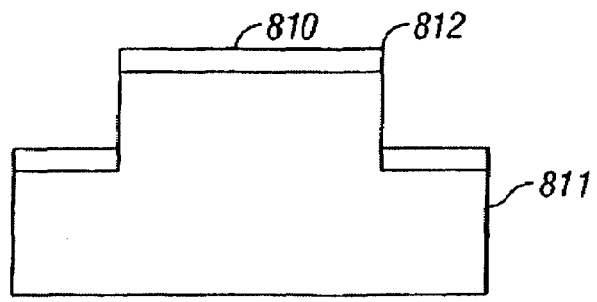

A first method of fabricating the wear gauge 300 may be understood with reference to FIGS. 7a-c. A ceramic (AlTiC) wafer is cut to form a rectilinear bar (quad section) 702 having a width 704 generally greater than the desired length of the wear gauge in the direction perpendicular to the tape motion. Narrow slots 705 are cut perpendicular to the end surface 706 of the quad section 702. The end surface 706 of the quad section is lapped and polished to form a flat wear surface 708 having a roughness preferably in the range 1-4 nm. A row slice 709 parallel to the plane of the wear surface 708 separates a wear gauge 710 block from the quad section 702. A grinding operation removes unwanted material 711 and forms the air-skiving edges 712 of the wear gauge. The bar is then cut to the desired length. A coating 714 of transparent material is formed on the wear surface 708 by a vacuum deposition process, such as sputter deposition, to complete the wear gauge block.

A second method of fabricating the wear gauge 300 may be understood with reference to FIGS. 8a-d. Starting with a blank wafer 802 of AlTiC, slots 804 are cut to create plateaus 806 having a width preferably in the range of 500-1000 microns and spaced 1-3 mm apart. The top surface 808 of the wafer is then polished to provide flat wear surfaces 810 on the plateaus 806 having a roughness of about 2 nm. The wafer is then sliced along the centers 809 of the slots 804 to create bars having the cross-section shown in FIG. 8d. The bars are then sliced into wear blocks 811 having the desired length for use as wear gauges. A coating 812 of transparent material is then vacuum deposited on the wear surfaces 810 to complete the fabrication process. This fabrication method is a low cost, batch process well-suited to mass production of standard wear gauges for the tape industry.

While the present invention has been particularly shown and described with reference to the preferred embodiments, it will be understood by those skilled in the art that various changes in form and detail may be made without departing from the spirit, scope and teaching of the invention. Accordingly, the disclosed invention is to be considered merely as illustrative and limited only as specified in the appended claims.

We claim:

1. A method of testing the wear of a wear gauge simulating a magnetic recording head at the interface of the recording head with a magnetic recording medium, the method comprising:
    mounting the wear gauge comprising a wear surface having first and second edges in a test fixture;
    positioning a tape and adjusting an overwrap angle at the first and second edges;
    choosing the tape tension, speed and runtime;
    running the tape in operational contact with the wear surface for the chosen runtime;
    inspecting the wear surface under white light illumination;
    recording locations of observed interferometric color changes on the wear surface; and
    converting color changes to thickness changes of a transparent coating on the wear surface.

2. The method of claim 1, further comprising:
    running profilometer scans across the wear surface.

3. The method of claim 1, wherein the overwrap angle is 1 degree.

4. The method of claim 1, wherein the coating is chosen from the group of materials consisting of $SiO_2$, $Al_2O_3$, amorphous carbon, and sapphire.

5. The method of claim 1, wherein the coating has a thickness in the range of 50-250 nm.

6. The method of claim 1, wherein the white light illumination is at normal incidence to the wear surface.

7. The method of claim 1, wherein the tape is run unidirectionally across the wear surface.

8. A method of making a wear gauge, comprising:
    obtaining a substrate wafer;
    cutting parallel uniformly spaced apart slots in a top surface of the wafer to create uniformly spaced apart plateaus;
    polishing the top surface of the wafer to provide flat wear surfaces on the plateaus;
    slicing the wafer along the centers of the slots to create bars;
    cutting the bars to a desired length; and
    depositing a coating of transparent material on the wear surfaces.

9. The method of claim 8, wherein the coating is chosen from the group of materials consisting of $SiO_2$, $Al_2O_3$, amorphous carbon, and sapphire.

10. The method of claim 8, wherein the coating has a thickness in the range of 50-250 nm.

11. The method of claim 8 wherein the substrate wafer is made of AlTiC.

12. A method of making a wear gauge, comprising:
    obtaining a substrate wafer;
    cutting the wafer to form a rectilinear bar;
    cutting two parallel spaced apart slots in an end surface of the bar, said slots perpendicular to the surface of the bar;
    lapping and polishing the end surface of the bar;
    slicing the bar parallel to the end surface;
    removing unwanted material outside the parallel spaced apart slots in the end surface; and
    depositing a coating of transparent material on the end surface.

13. The method of claim 12, wherein the coating is chosen from the group of materials consisting of $SiO_2$, $Al_2O_3$, amorphous carbon, and sapphire.

14. The method of claim 12, wherein the coating has a thickness in the range of 50-250 nm.

15. The method of claim 12 wherein the substrate wafer is made of AlTiC.

16. A device for simulating wear of a system component at a working surface at the interface of the component with an abrasive medium, said device comprising:
    a wear gauge block having a wear surface that substantially approximates the dimensions, contour and surface finish of the working surface of the component; and
    a coating of transparent material on said wear surface, said coating having a front surface and a rear surface spaced apart a thickness in a range suitable for causing interference of incident visible light reflected from the front surface with light reflected from the rear surface.

* * * * *